United States Patent [19]
Krug et al.

[11] Patent Number: 5,475,158
[45] Date of Patent: Dec. 12, 1995

[54] PREPARATION OF CYCLOALKANOLS

[75] Inventors: Thomas Krug, Frankenthal; Rolf Fischer, Heidelberg; Rolf Pinkos, Bad Duerkheim, all of Germany

[73] Assignee: BASF Aktiengesellschaft, Ludwigshafen, Germany

[21] Appl. No.: 159,706

[22] Filed: Dec. 1, 1993

Related U.S. Application Data

[63] Continuation of Ser. No. 996,396, Dec. 23, 1992, abandoned.

[30] Foreign Application Priority Data

Dec. 24, 1991 [DE] Germany .................. 41 42 944.3

[51] Int. Cl.⁶ .................. C07C 29/20; C07C 53/10
[52] U.S. Cl. .................. 568/835; 568/821; 568/838; 562/607; 562/609
[58] Field of Search .................. 562/607, 609; 568/835, 821, 838

[56] References Cited

U.S. PATENT DOCUMENTS 4,642,166  2/1987  Berg et al. .
4,786,370  11/1988  Berg et al. .

FOREIGN PATENT DOCUMENTS 3116832  2/1982  Germany .................. 562/607
7004497  3/1970  Netherlands .

OTHER PUBLICATIONS

Chem Abstracts, vol. 76, 126, 476 X (1971).

*Primary Examiner*—Alan Spegel
*Attorney, Agent, or Firm*—Keil & Weinkauf

[57] ABSTRACT

A process for the preparation of cycloalkanols by the hydrolysis of cycloalkyl $C_1$–$C_4$ fatty acid esters, which comprises the following steps:

a) reaction of cycloalkyl $C_1$–$C_4$ fatty acid esters with water at a temperature of from 30° to 250° in the liquid phase yielding a reaction mixture consisting of cycloalkyl $C_1$–$C_4$ fatty acid esters, cycloalkanol, $C_1$–$C_4$ fatty acids, and water.

b) separation of the reaction mixture obtained in stage a) at a temperature of from 0° to 200° C. into a top phase consisting substantially of cycloalkanol and cycloalkyl $C_1$–$C_4$ fatty acid esters and a bottom phase consisting substantially of water and $C_1$–$C_4$ fatty acids.

c) separation of cycloalkanol from the top phase obtained in stage b) by distillation and recycling unconverted cycloalkyl $C_1$–$C_4$ fatty acid esters to stage a).

9 Claims, No Drawings

PREPARATION OF CYCLOALKANOLS

This application is a continuation of application Ser. No. 07/996,396, filed on Dec. 23, 1992, now abandoned.

The invention relates to a process for the preparation of cycloalkanols by the hydrolysis of cycloalkyl $C_1$–$C_4$ fatty acid esters.

NL-A 7,004,497 discloses that cyclohexanol can be obtained from cyclohexyl ester by alkaline hydrolysis. A drawback of this method, as with alkaline saponification in general, is that the carboxylic acid occurs in the form of a salt, and must therefore be recovered by expensive measures. The process also suffers from the drawback that considerable amounts of waste-waters which are below specification requirements are formed.

In another process, described in Polish Patent 63,551 (Chemical Abstracts, Vol 76, Ref 126, 476x) cyclohexyl esters are dissociated using nitric acid or sulfuric acid. The cyclohexanol is obtained by energy-consuming steam distillation.

It is thus an object of the invention to provide a process for the preparation of cycloalkanols by the hydrolysis of cycloalkyl $C_1$–$C_4$ fatty acid esters, in which a high degree of selectivity toward the cycloalkanols and fatty acids is achieved, little cycloalkene is formed as by-product, the acids are easy to recover, and the amount of under-spec waste-waters formed is reduced to a minimum.

This object is achieved in a process for the preparation of cycloalkanols by the hydrolysis of cycloalkyl $C_1$–$C_4$ fatty acid esters, which comprises the following steps:

a) reaction von cycloalkyl $C_1$–$C_4$ fatty acid esters with water at a temperature of from 30° to 250° C. in the liquid phase yielding a reaction mixture consisting of cycloalkyl $C_1$–$C_4$ fatty acid esters, cycloalkanol, $C_1$–$C_4$ fatty acids, and water.

b) separation of the reaction mixture obtained in stage a) at a temperature of from 0° to 200° C. into a top phase consisting substantially of cycloalkanol and cycloalkyl $C_1$–$C_4$ fatty acid esters and a bottom phase consisting substantially of water and $C_1$–$C_4$ fatty acids.

c) separation of cycloalkanol from the top phase obtained in stage b) by distillation and recycling unconverted cycloalkyl $C_1$–$C_4$ fatty acid esters to stage a).

Our novel process has the advantage that it achieves high selectivity toward cycloalkanol, and little cycloalkene is formed. Another advantage of the novel process is that it can be easily carried out continuously on at industrial scale, and only a small amount of under-spec waste-water is formed.

In a first step a), cycloalkyl $C_1$–$C_4$ fatty acid esters are reacted with water at a temperature of from 30° to 250° C. in the liquid phase yielding a reaction mixture essentially consisting of cycloalkyl $C_1$–$C_4$ fatty acid ester, cycloalkanol, fatty acid, and water.

It is preferred to start from $C_1$–$C_4$ fatty acid esters of cycloalkanols having from 5 to 8 carbon atoms in the ring, in particular, from their fatty acid esters having 1 or 2 carbon atoms. Cyclohexyl formate or acetate has attained special industrial significance. Suitable cycloalkyl $C_1$–$C_4$ fatty acid esterts are, e.g., cyclopentyl formate, cyclohexyl formate, cyclooctyl formate, cyclopentyl acetate, cyclohexyl propionate, and cyclooctyl acetate. The use of cyclohexyl formate yields particularly satisfactory results. It is obvious that the preferred cycloalkanols are obtained from the preferred cycloalkyl fatty acid esters.

Usually, there are used, for each mole of cycloalkyl $C_1$–$C_4$ fatty acid ester, from 0.1 to 100 mol of water, advantageously from 1 to 30 and preferably from 2 to 10 mol of water.

The conversion is carried out at a temperature of from 30° to 250° C. It is advantageous to maintain a temperature of from 60° to 200° C. and preferably from 70° to 160° C. It is possible to carry out the conversion under standard pressure conditions, under elevated pressure or under slightly reduced pressure, for example, under a pressure of from 0.3 to 20 bar and preferably from 0.8 to 10 bar. The pressure and temperature conditions are chosen such that the starting materials and end products are in the liquid phase.

It is usual to maintain residence time in stage a) of from 5min to 300min. Satisfactory results have been obtained using residence times ranging from 15 to 120 min.

The hydrolysis of the cycloalkyl $C_1$–$C_4$ fatty acid esterts can be carried out autocatalytically or with the addition of an acidic catalyst. The conversion is carried out using, advantageously, a strongly acidic catalyst. Suitable acidic catalysts are zeolites, acidic ion exchangers, heteropoly acids, acidic and superacidic metal oxides, which may optionally be doped with anions such as $SO_4^{2-}$, and inorganic or organic acids.

Preferred zeolites are those from the mordenite group or fine-pored zeolites of the erionite, chabazite or faujasite species, e.g. X-, Y- or L-type zeolites. Also suitable are ultrastable zeolites from the faujasite group, which are dealuminated.

Particularly preferred substances are zeolites having a pentasile structure, such as ZSM 5 ZSM 11 and ZBM 10. These have in common, as main building block, a five-membered ring composed of $SiO_2$ tetrahedra, they exhibit a high ratio of silicon dioxide to aluminum oxide, and they have pore sizes which lie between those of the zeolites of type A and those of type X or Y. Good results have been obtained using zeolites in which the ratio of silicon dioxide to aluminum oxide is smaller than 100: 1. The zeolites can be present entirely or partially in the H-form.

Preferred acidic ion exchangers are cross-linked polystyrenes containing sulfonic acid groups or polyperfluoroalkanesulfonic acids.

Preferred heteropoly acids are poly acids of molybdenum or tungsten with phosphoric acid, telluric acid, selenic acid, arsenic acid, silicic acid or, in particular, with phosphoric acid. The following are examples thereof: dodecatungstatophosphoric acid or dodeca-molybdatophosphoric acid. The protons of the heteropoly acids can be partially replaced by metal ions. Alkali-metal and alkaline earth metal ions are preferred.

Suitable acidic metal oxides are, for example, silicon dioxide, aluminum oxide, zirkonium dioxide, titanium dioxide or tin dioxide. To increase their acid strength, such metal oxides can be treated prior to use with, say, sulfuric acid.

Suitable acids are for example mineral acids such as sulfuric acid or phosphoric acid, and also organic acids such as sulfonic acids or carboxylic acids. Preferably, use is made of the fatty acids of the ester used, in particular formic acid.

The ratio by weight of catalyst used to cyclic ester is usually from 0:1 to 20:1 and preferably from 0:1 to 5:1 and more preferably from 0:1 to 1:1.

The cycloalkyl $C_1$–$C_4$ fatty acid esters used can already contain the corresponding cycloalkanol as by-product, for example in a concentration of up to 50 mol %, in particular of up to 10 mol %and advantageously of up to 5 mol %.

There is obtained a reaction mixture which consists substantially of cycloalkanol, cycloalkyl $C_1$–$C_4$ fatty acid esters, $C_1$–$C_4$ fatty acids, and water, and which can optionally contain small amounts of cyclohexene.

In step b), the reaction mixture obtained in stage a) is separated at a temperature of from 0° to 200° C. optionally under an elevated pressure of, say, from 1 to 10 bar and preferably from 1 to 5 bar, into a top phase consisting substantially of cycloalkanol and cycloalkyl $C_1$–$C_4$ fatty acid ester and a bottom phase consisting substantially of water and fatty acid.

To ensure formation of the phases, it is advantageous to maintain a temperature of from 20° to 140° C. The separation of the phases takes place, for example, in a phase separator. It has proven advantageous to add water to assist phase separation, eg, from 5 to 20 wt %, based on the mixture to be separated.

The top phase essentially consists of cycloalkanol and cycloalkyl $C_1$–$C_4$ fatty acid esters and contains, in addition to minor amounts of water, $C_1$–$C_4$ fatty acid and cyclohexene as by-products. The bottom phase essentially consists of water and $C_1$–$C_4$ fatty acids and additionally contains small amounts of cycloalkanol and cycloalkyl $C_1$–$C_4$ fatty acid ester.

Cycloalkanol is separated from the top phase by distillation. It is advantageous to treat the top phase with water, in order to remove acids. Further purification takes place advantageously by distillation, eg in a column equipped with from 20 to 30 theoretical trays. Water and residues of fatty acids are usually removed as overheads, a mixture of cycloalkanol and cycloalkyl fatty acid ester is removed as azeotrope via a side outlet, and pure cycloalkanol is withdrawn at the bottom. If no use is made of a side outlet, there are usually obtained overheads consisting of water, fatty acid, cycloalkanol, and cycloalkyl ester, which mixture can be recycled to the up-stream phase separator, whilst pure cycloalkanol accumulates at the base.

The bottom phase, which consists substantially of water and fatty acid, is advantageously extracted by a method such as is described, for example, in U.S. Pat. Nos. 4,642,166 and 4,786,370. The water formed is advantageously recycled to the hydrolysis stage a), whilst fatty acids can bemused for the preparation of cyclohexyl esters.

The cycloalkanols produced by the process of the invention, e.g., cyclohexanol, are valuable starting points for fiber precursors.

The process of the invention may be illustrated by the following examples:

EXAMPLE 1

1.29 g of cyclohexyl formate and 0.85 g of water were heated at 150° C. in an autoclave having a capacity of 25 mL, with stirring over a period of 2h. The pressure was 3.2 bar. The reaction mixture comprised two-phases both during and after the reaction. For analysis purposes, the two-phase effluent was homogenized with acetone. There were obtained, in addition to unconverted cyclohexyl formate, 6.5 mol %of cyclohexanol and 0.6 mol %of cyclohexene. Other by-products were not found. Quantitative analysis was carried out using GC (internal standard).

EXAMPLE 2

Using a procedure analogous to that employed in Example 1, the same reaction mixture was stirred with the addition of 0.23 g of formic acid at 110° C. over a period of 2 h. Following homogenization of the two-phase effluent, there were obtained, in addition to unconverted cyclohexyl formate, 54 mol % of cyclohexanol. No by-products could be detected.

EXAMPLE 3

Using a procedure analogous to that employed in Example 1, 1.28 g of cyclohexyl formate, 0.85 g of water, and 0.1 g of molybdatophosphoric acid were reacted at 90° C. over a period of 30 min.

Following homogenization there were obtained, in addition to unconverted cyclohexyl formate, 62.7mol % of cyclohexanol. The only by-product formed comprised 0.1 mol % of cyclohexene.

EXAMPLE 4

Using a procedure analogous to that employed in Example 3, 61.9mol % of cyclohexanol were obtained using the same technique, but at 110° C. The only by-product was cyclohexene in a concentration of 0.7 %.

EXAMPLE 5

Using a procedure analogous to that employed in Example 1, 1.28 g of cyclohexyl formate, 2.70 g of water, and 0.5 g of sulfonated polytetrafluoroethylene were heated at 110° C. over a period of 2 h. Following homogenization of the liquid phase there were obtained, in addition to unconverted cyclohexyl formate, 75.8 mol % of cyclohexanol. The only by-product formed was cyclohexene in a concentration of 0.9 mol %.

EXAMPLE 6

Using a procedure analogous to that employed in Example 1, 1.28 g of cyclohexyl formate, 1.8 g of water, and 0.5 g of a sulfonated polytetrafluoroethylene were heated at 110° C. over a period of 2 h. Following separation of the catalyst and homogenization with acetone there were obtained, in addition to unconverted cyclohexyl formate, 70.2 mol % of cyclohexanol, and the only by-product was 1.8 mol % of cyclohexene.

EXAMPLE 7

Using a procedure analogous to that employed in Example 1, 7.6 g of water, 0.2 g of formic acid, 1.4 g of cyclohexanol, and 10.8 g of cyclohexyl formate were reacted at 130° C. over a period of 2 h. The two-phase effluent was separated into the individual phases in a phase separator.

In the top phase there were 0.02 g of cyclohexene, 6.90 g of cyclohexanol, 3.50 g of cyclohexyl formate, from 1.3 to 1.4 g of formic acid, and 1 g of water (the formic-acid content was determined potentiometrically, the water content by the Karl-Fischer method).

In the bottom phase there were 0.20 g of cyclohexanol, 0.02 g of cyclohexyl formate, from 1.4 to 1.5 g of formic acid, and ca 5 g of water.

EXAMPLE 8

Using a procedure analogous to that employed in Example 1, 1.8 g of cyclohexyl formate, 3.57 g of water, and 0.11 g of phosphoric acid (85 % strength) were heated at 110° C. 2 h. The two-phase effluent was separated into the individual phases. In the top phase (3.80 g) there were 75.3 mol % of cyclohexanol and 18.2 mol % of cyclohexyl formate. In the bottom phase (1.68 g) there were 6.5mol % of cyclohexanol. Cyclohexene was not found.

EXAMPLE 9

Using a procedure analogous to that employed in Example 1, 2.0 g of cyclohexyl acetate, 1.16 g of water and 0.5 g of cross-linked polystyrene were reacted at 120° C. with sulfonic acid groups over a period of 30 min. The two-phase effluent was homogenized. In addition to unconverted cyclohexyl acetate, 16.7 mol % of cyclohexanol were found. The only by-product was cyclohexene in a concentration of 0.6 mol %.

EXAMPLE 10

Using a procedure analogous to that employed in Example 1, 115 g of cyclohexyl formate, 5 g of molybdatophosphoric acid, and 240 g of water were reacted at 90° C. over a period of 1 h. Following cooling of the reaction mixture to 25° C., the top phase (105 g) was passed to distilling equipment. At 1013 mbar and a base temperature of 170° C., 50 g of a two-phase mixture distilled off (15 wt % of cyclohexanol, 66 wt % of cyclohexyl formate, 2 wt % of cyclohexene, 17 wt % of water, and formic acid). The residue weighed 55 g. As determined by GC-analysis, this residue contained 98 % of cyclohexanol (60 % yield). The bottom phase substantially consisted of water, formic acid and catalyst.

We claim:

1. A process for the preparation of cycloalkanols by the hydrolysis of cycloalkyl $C_1$–$C_4$ fatty acid ester comprising the following steps:

a) reacting cycloalkyl $C_1$–$C_4$ fatty acid esters with water at a temperature of from 30° to 250° C. in the liquid phase to yield a reaction mixture consisting of cycloalkyl $C_1$–$C_4$ fatty acid esters, cycloalkanol, $C_1$–$C_4$ fatty acids, and water b) separating the reaction mixture obtained in stage a) into physically distinct and mechanically separable phases at a temperature of from 0° to 200° C. into a top phase consisting essentially of cycloalkanol and cycloalkyl $C_1$–$C_4$ fatty acid esters and a bottom phase consisting essentially of water and $C_1$–$C_4$ fatty acids, and c) separating cycloalkanol from the top phase obtained in stage b) by distillation, leaving unconverted cycloalkyl $C_1$–$C_4$ fatty acid esters in the top phase, and recycling the unconverted cycloalkyl $C_1$–$C_4$ fatty acid esters to stage a).

2. A process as claimed in claim 1, wherein from 1 to 30 mol of water are included for each mole of cycloalkyl $C_1$–$C_4$ fatty acid ester.

3. A process as claimed in claim 1, wherein the catalyst is selected from the group consisting of zeolites, acidic ion exchangers, heteropoly acids, acidic metal oxides, mineral acids, and organic carboxylic and sulfonic acids.

4. A process as claimed in claim 1, wherein a temperature of from 70° to 160° C. is maintained in stage a).

5. A process as claimed in claim 1, wherein the residence time in stage a) is adjusted to from 15 to 120 min.

6. A process as claimed in claim 1, wherein, in stage b), a temperature of from 20° to 140° C. is maintained during phase separation under a pressure of from 1 to 5 bar.

7. A process as claimed in claim 1, wherein water is added, in stage b), for phase separation.

8. A process as claimed in claim 1, wherein the top phase obtained in stage b) is distilled in a column, from which a mixture of fatty acid and water is removed at the top, an azeotropic mixture of cycloalkanol and cycloalkyl $C_1$–$C_4$ fatty acid ester in the middle portion, and cycloalkanol at the bottom.

9. A process as claimed in claim 1, wherein the starting material for the process is a cyclohexyl $C_1$ or $C_2$ fatty acid ester.

* * * * *